United States Patent
Xia et al.

(10) Patent No.: US 10,428,648 B2
(45) Date of Patent: Oct. 1, 2019

(54) DOWNHOLE FORMATION FLUID VISCOMETER SENSOR

(71) Applicant: HALLIBURTON ENERGY SERVICES, INC., Houston, TX (US)

(72) Inventors: Hua Xia, Huffman, TX (US); Lizheng Zhang, Humble, TX (US); Robert Atkinson, Conroe, TX (US); Nestor Rodriguez, Shenandoah, TX (US); Christopher Michael Jones, Houston, TX (US); Darren Gascooke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 323 days.

(21) Appl. No.: 15/504,911

(22) PCT Filed: Sep. 16, 2014

(86) PCT No.: PCT/US2014/055924
§ 371 (c)(1),
(2) Date: Feb. 17, 2017

(87) PCT Pub. No.: WO2016/043722
PCT Pub. Date: Mar. 24, 2016

(65) Prior Publication Data
US 2017/0241262 A1    Aug. 24, 2017

(51) Int. Cl.
| | | |
|---|---|---|
| *E21B 49/08* | (2006.01) | |
| *G01N 11/10* | (2006.01) | |
| *G01N 11/16* | (2006.01) | |

(52) U.S. Cl.
CPC ............ *E21B 49/08* (2013.01); *E21B 49/081* (2013.01); *G01N 11/10* (2013.01); *G01N 11/16* (2013.01); *E21B 2049/085* (2013.01)

(58) Field of Classification Search
CPC ... E21B 49/08; E21B 2049/085; G01N 11/10; G01N 11/16
See application file for complete search history.

(56) References Cited

U.S. PATENT DOCUMENTS

| | | |
|---|---|---|
| 6,070,457 A | 6/2000 | Robinson |
| 7,574,898 B2 | 8/2009 | Harrison et al. |
| | (Continued) | |

FOREIGN PATENT DOCUMENTS

WO    2012016045    2/2012

OTHER PUBLICATIONS

Extended European Search Report for EP EP14901885 dated Mar. 20, 2018.
(Continued)

*Primary Examiner* — Paul M. West
(74) *Attorney, Agent, or Firm* — Locke Lord LLP (57) ABSTRACT

A downhole formation fluid viscometer sensor and method therefor include a viscometer sensing package, a flexible diaphragm, a magnet and electric coil, and a signal pickup assembly. The viscometer sensor may also include a first cavity and a second cavity for mechanical and electric energy transfer. The magnet and electric coil may be driven by external alternating current to generate an electromagnetic force. Silicon oil may be used to fill the first cavity and/or a pressure balance hole may connect the first cavity to an external area. The diaphragm may be a titanium alloy and a ferromagnetic magnet may be attached to the diaphragm. The diaphragm preferably has a thickness from about 0.030 to about 0.040 inches and the magnet and electric coil can propel the diaphragm to vibrate at a frequency from 0 to 100 kHz. Formation fluid viscosity is (Continued)

determined using resonant frequency linewidth, with contributions from the sensor package intrinsic properties removed.

16 Claims, 7 Drawing Sheets

(56) References Cited

U.S. PATENT DOCUMENTS

| | | |
|---|---|---|
| 7,784,330 B2 | 8/2010 | Angelescu et al. |
| 7,874,199 B2 | 1/2011 | Chaudoreille et al. |
| 8,316,715 B2 * | 11/2012 | Jacob .................... G01H 11/02 |
| | | 73/643 |
| 8,392,121 B2 | 3/2013 | Zamora et al. |
| 8,484,003 B2 | 7/2013 | Hsu et al. |
| 8,485,018 B2 | 7/2013 | Kawamura et al. |
| 2003/0230136 A1 | 12/2003 | Wright |
| 2008/0055013 A1 | 3/2008 | Alvarez |
| 2009/0044953 A1 | 2/2009 | Sheth et al. |
| 2009/0301210 A1 * | 12/2009 | Becher ................. G01L 9/0055 |
| | | 73/715 |
| 2011/0030455 A1 | 2/2011 | Matsumoto et al. |
| 2011/0296925 A1 * | 12/2011 | Miesel ................. G01L 9/0072 |
| | | 73/718 |
| 2012/0085161 A1 | 4/2012 | Kumar |

OTHER PUBLICATIONS

Lee, Chang; PCT Search Report for PCT Application No. PCT/US2014/055924 dated Jun. 18, 2015.
Lee, Chang; PCT Written Opinion for PCT Application No. PCT/US2014/055924 dated Jun. 18, 2015.

* cited by examiner

DOWNHOLE FORMATION FLUID VISCOMETER SENSOR

FIELD OF INVENTION

The embodiments disclosed herein relate generally to fluid thermophysical properties sensing device and more specifically to downhole hydrocarbon fluid viscosity in-situ measurement for openhole formation fluid logging analysis.

BACKGROUND OF INVENTION

Hydrocarbon fluid thermophysical property measurement under native or in-situ conditions is a critical part of estimating the economic values of a subterranean formation reservoir. Among the fluid thermophysical properties of interest is viscosity, which is the characteristic of a fluid to dissipate energy. The viscosity of a formation fluid can help identify the type of petroleum (e.g., heavy oil, medium oil, light oil) present in the formation. However, the viscosity of a hydrocarbon fluid is also strongly dependent upon temperature and pressure. Viscosity measurements may be performed by exposing a vibrating tube or wire-based sensing device to a downhole fluid to be measured and causing the sensing device to vibrate within the fluid. By measuring the loading effects of the fluid on the vibration of the tubing or the wire, the viscosity of the downhole fluid may be determined. On the other hand, hydrocarbon producing wells may contain different phases and mixtures, each having different thermophysical properties. During petroleum production operations, thermophysical properties, such as density and viscosity, and other parameters often affect production efficiency. High viscosity hydrocarbon fluid production may require external heating to reduce the viscosity of the fluid and enable fluid transport from one place in the reservoir to the well location. It is thus desirable to be able to measure viscosity properties during wireline logging service or during the production process. The obtained formation fluid viscosity property can be used for wellbore completion, production efficiency control, and optimization.

Viscosity is the internal resistance to flow exhibited by a fluid, and is a key fluid parameter for a variety of fluids, including lubricants, adhesives, paints, oils, tars, electrophoresis gels, syrups and fuels. Various methods have been developed to measure viscosity, including capillary force, moving paddles, blades, vibrating tuning forks, and hollow tubes or cantilevers immersed in a fluid. More recently, rheometers and viscometers have been developed with a vibrating micro-machined silicon cantilever that is immersed in the fluid of interest, with the resultant damping of the cantilever vibration being used to indicate viscosity. The above-noted solutions have performed satisfactorily in the laboratory, but have proven challenging to implement in a downhole high-temperature and high-pressure (HTHP) harsh environment. It is therefore desirable to have a high-sensitivity viscosity sensing device that can reliably operate under downhole harsh environmental conditions.

DETAILED DESCRIPTION OF DISCLOSED EMBODIMENTS

As an initial matter, it will be appreciated that the development of an actual, real commercial application incorporating aspects of the disclosed embodiments will require many implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time.

While a developer's efforts might be complex and time-consuming in an absolute sense, such efforts would nevertheless be a routine undertaking for those of skill in this art having the benefit of this disclosure.

It should also be understood that the embodiments disclosed and taught herein are susceptible to numerous and various modifications and alternative forms. Thus, the use of a singular term, such as, but not limited to, "a" and the like, is not intended as limiting of the number of items. Similarly, any relational terms, such as, but not limited to, "top," "bottom," "left," "right," "upper," "lower," "down," "up," "side," and the like, used in the written description are for clarity in specific reference to the drawings and are not intended to limit the scope of the exemplary embodiments.

One embodiment disclosed herein relates to a sensor for a viscometer capable of measuring formation fluid viscosity properties. The viscometer sensor includes an electromagnetic coupling device having a ferromagnetic material-based first magnet attached to a diaphragm and sealed in a first cavity, and a second magnet having an electrical coil wound around it and sealed in a second cavity. The second magnet and electrical coil assembly is configured to electromagnetically drive an oscillation or vibration of the first magnet across a gap or barrier between the first and second cavities. The oscillation of the first magnet causes displacement of the attached diaphragm that may be detected by induced eddy current effect. The second magnet and electric coil assembly may be further configured to produce periodic or non-periodic electromagnetic driving force for contactless pushing and pulling of the first magnet and/or the attached diaphragm. The viscometer sensor may further include the use of silicon oil or the like filling the first cavity for creating a pressure differential on the two sides of the diaphragm, a pressure balance hole for balancing out the pressure between the interior and exterior of the first cavity, and/or a flexible diaphragm made from titanium alloy and having the first ferromagnetic magnet attached. This viscometer sensor may further include a processor configured or programmed to determine time-domain amplitude attenuation of the diaphragm under a non-periodic pulsed current driving signal.

Another embodiment disclosed herein relates to a method of electromechanically driving the viscometer sensor for measuring fluid viscosity. The method includes extracting a system quality factor from the measured fluid viscosity, and correlating the measured resonance linewidth with the viscosity. The viscometer sensor is driven to vibrate with a pair of magnets having a first magnet in a first cavity and a second magnet with an electrical coil in a second cavity. The method may also include conveying an electrical current from an external source to the electrical coils, and using the resulting electrical and mechanical energies to produce diaphragm vibration. As well, the method may include using the same electrical coils to pick up vibrating diaphragm dynamic response characteristic by detecting induced eddy current variation. The method may further include using periodic and non-periodic electric current driving sequences to induce natural diaphragm vibration. The method may still further include modulating the external current in the time-domain for measuring formation fluid viscosity using induced damping effect. The method may also further include modulating the external current in the frequency-domain for inducing maximum vibrating tube amplitude using a carrier frequency from a few kilohertz, for example, to a few tens of kilohertz range to determine a formation fluid viscosity.

A further embodiment disclosed herein relates to a method of measuring fluid viscosity, including the steps of exciting a vibration in the diaphragm at its resonant frequency by an electromagnetic force produced by exciting current, measuring a natural damping amplitude as a function of time after the external exciting force is removed, measuring a corresponding voltage decay signal, and determining a vibration resonant frequency using a Fast Fourier Transform based algorithm or process. In these embodiments, the sensor may include a vibrating diaphragm, a ferromagnetic material-based magnet attached to the diaphragm in a first cavity having a differential pressure balance hole, and a magnet/electrical coil assembly in a second cavity, wherein a signal indicative of viscosity is picked up by induced eddy current effect from the first magnet surface. The method may also include sensing downhole formation fluid kinematic viscosity and dynamic viscosity by combining the viscosity sensor with a density sensor, preferably in open hole wireline logging environments or heavy oil production process for providing multi-parameter in-situ fluid thermophysical property analyses.

The particular design of the viscometer sensor package depends in large part upon the difference in pressure on the two sides of the diaphragm, that is, the pressure difference between the sensor's internal cavity and the external environment. There is a tradeoff between pressure differential and diaphragm thickness, which may affect the vibration frequency and survivability of the sensor package in downhole conditions. For example, when a diaphragm is sealed under vacuum conditions, the diaphragm has to sustain at least 20 kpsi of pressure, which requires a thicker diaphragm. Using a vacuum sealed cavity also requires a high driving power to excite vibration on the thicker diaphragm, which may be difficult due to magnet size and maximum driving current limitations. However, for a few hundreds of psi or less pressure difference across the cavity, the diaphragm thickness can be greatly reduced to enable a high level of sensitivity to small viscosity variation.

The fluid viscosity is measured by fluid friction induced damping that can attenuate vibrating diaphragm amplitude within a limited time interval. The diaphragm vibration disclosed here is produced by driving a first magnet using a second magnet and electrical coil assembly that induces repulsive force on the first magnet under a modulated pulsed current driving signal. This electromagnetic force-driven first magnet is driven directly and the diaphragm vibrations are driven indirectly. Under appropriate driving frequency or carrier frequency, the diaphragm vibration can reach a maximum amplitude at its natural vibration frequency. Following removal of the external driving force, the natural decay of the diaphragm displacement amplitude provides simple viscosity detection in the time domain where the diaphragm displacement amplitude decays as a result of the fluid friction effect or elastic energy dissipation process. The magnet and electrical coil assembly may be modulated in a time sequence such that a pulse of current is sent to the assembly to excite the diaphragm to vibrate and then slowly attenuate. The displacement or amplitude decay data are transmitted via a telemetry terminal for processing. The next pulse of the driving pulse is then sent to the magnet and electric coil assembly, and new amplitude decay data is measured for continuous formation fluid sampling analysis.

Accordingly, in one implementation, the disclosed viscometer sensor is an electromagnetic mechanical vibration transducer that has a vibrating diaphragm in front of the sensor package for measuring fluid friction-induced damping effect, driven by both time and frequency modulated electromagnetic force under periodic or non-periodic operation mode. The kinematic viscosity may be determined by resonant mode frequency, f, and quality factor, Q, from a diaphragm force-free attenuation response curve.

Figure 1A:
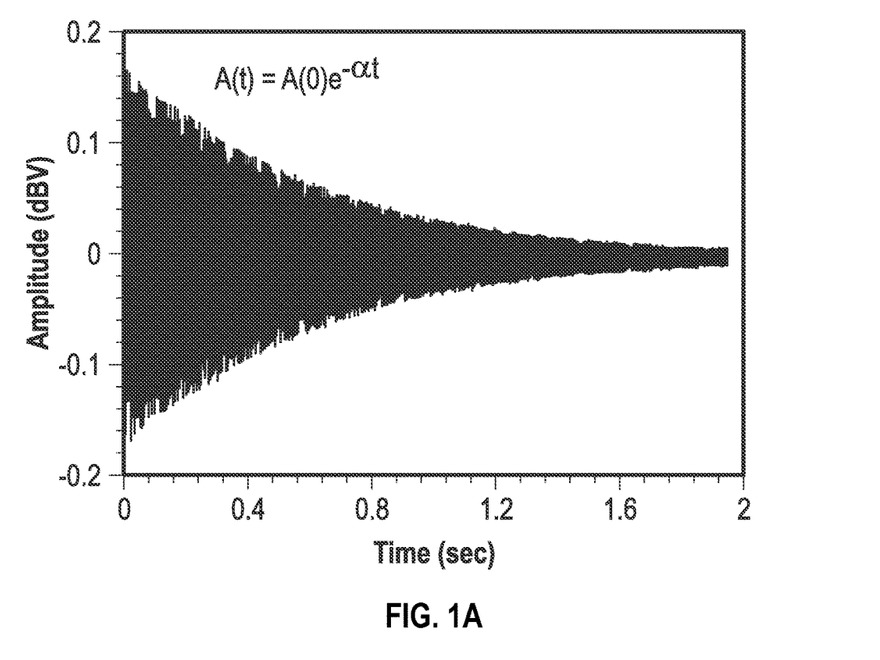
FIGS. 1A and 1B show time-domain diaphragm decay amplitude and resonant frequency characteristics under pulsed electric driving condition, respectively.
Figure 1B:
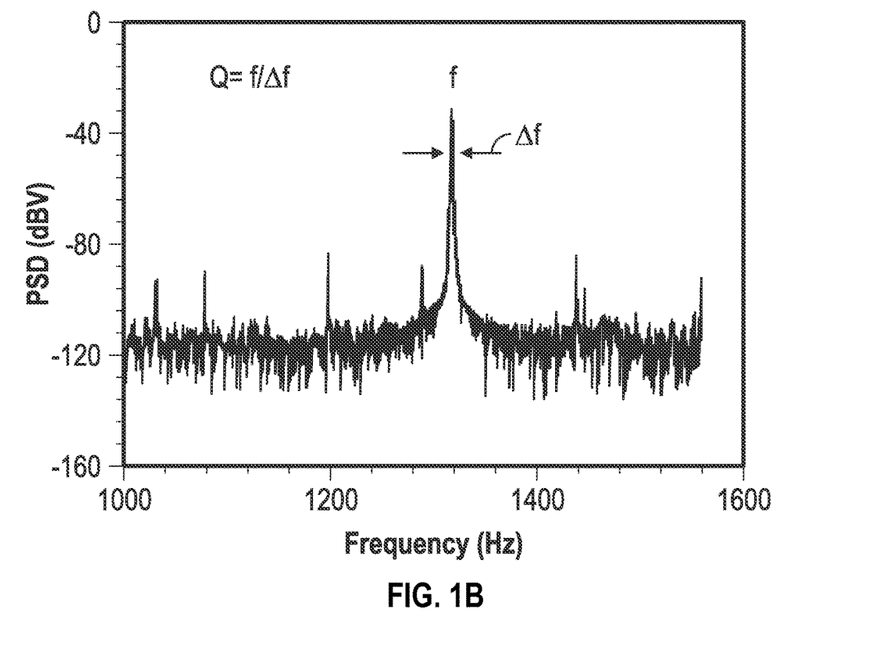

FIGS. 1A and 1B show a time-domain diaphragm vibration amplitude decay and resonant frequency characteristics under diaphragm force-free attenuation condition, where the vertical axis in FIG. 1A is amplitude in dBV and the horizontal axis is time in seconds, and the vertical axis in FIG. 1B is the power spectral density (PSD) in dBV and the horizontal axis is frequency in Hz. Viscosity related friction attenuates the vibration amplitude, namely, A(t), while the power spectral density can be used to extract quality factor, $Q=f/\Gamma$, and resonant frequency value, f, or peak linewidth, $\Gamma$. As a factor, all fluids have different resistance to flow, and the so-called dynamic viscosity $\eta$ is determined by the ratio of shear stress and shear rate. When the density q of the fluid is known, kinematic viscosity is simply determined by $\eta/q$. The flow resistance and resultant diaphragm vibration amplitude decay will reduce a vibration system's quality factor Q, which may be seen from the resonant frequency peak width $\Gamma$, measured at 3 dB peak amplitude. The methods for determining the kinematic viscosity and dynamic viscosity are summarized as follows.

First, a single pulse electric driving signal is introduced to the sensor and the transient alternating current produces a magnetic field that will propel the magnet in the first cavity to oscillate with the driving signal's modulation frequency. The oscillation causes the diaphragm to vibrate. A known testing fluid may be used and the alternating driving current adjusted until the diaphragm reaches a desired amplitude and frequency. After the diaphragm vibration reaches a desired amplitude and frequency, the external electric driving force is withdrawn and the diaphragm is allowed to vibrate naturally. Viscosity induced damping effect will eventually dissipate all the kinetic energy of the diaphragm.

In one embodiment, the time-domain decay of the diaphragm amplitude is measured using an interval ranging from 0.5 to 1 second. In another embodiment, the time-domain diaphragm amplitude decay is measured using an interval ranging from 0 to 2 seconds. Alternative interval ranges also may be used, but shorter data acquisition interval may be preferred in order to effectively reduce telemetry data transmission time.

The diaphragm vibrating amplitude is then fitted to a generic function, such as A(t)=A(0)·exp(−αt), where α is a decay parameter and may be determined by both fluid property and sensor package material property, and A(0) is the initial diaphragm vibrating amplitude. The obtained time-domain amplitude data is processed using a Fast Fourier Transform algorithm. Power spectral density data may be used to find the resonant peak frequency and shape in order to determine the resonant frequency f and peak linewidth Γ. The measured Q factor may be defined as $Q_{Meas}(T,P) = f_{Meas}(T,P)\gamma_{Meas}(T,P)$, where $\Gamma_{Meas}(T,P)$ is associated with the full width at half max (FWHM) of the resonant peak when the temperature is T and pressure is P. This system quality factor, $Q_{Meas}$, consists of fluid $Q_{fluid}$ and viscometer sensor $Q_S$, and can be described by:

$$\frac{1}{Q_{Meas}(T,P)} = \frac{1}{Q_{fluid}(T,P)} + \frac{1}{Q_S(T,P)}, \quad (1)$$

where $Q_S(T, P)$ is related to the viscometer sensor package contribution to the measured total system quality factor $Q_{Meas}(T, P)$.

For a preferred light-damping system, the linewidth variation of the resonant peak from the power spectral density data may be directly attributed to the fluid friction effect. However, the embodiments disclosed herein uses a metallic material having a temperature-dependent Young modulus. When the viscometer sensor is operated under elevated temperatures, the system quality factor will be intrinsically changed as a function of the temperature in some cases, and as a function of both temperature and pressure in real downhole cases. The viscosity analysis can be based on a differential linewidth, $\Delta\Gamma = \Gamma_{Meas}\gamma^*\Gamma_S(T,P)$, which may effectively remove the linewidth variation from intrinsic damping contributions of the sensor package itself. If the frequency response of the system $f_{Meas}(T, P)$ and viscometer sensor $f_S(T,P)$ are known, the viscosity can be calculated by:

$$Ln(\eta(T, P)) = A + B * \left[\Gamma_{Meas}(T, P) - \frac{f_{Meas}(T, P)}{f_S(T, P)} \cdot \Gamma_S(T, P)\right], \quad (2)$$

where A and B are calibration constants.

Furthermore, the kinematic viscosity can be simply determined by:

$$v(T,P) = \eta(T,P)/q(T,P), \quad (3)$$

where density Q is measured from a density sensor at the same location. The calculated kinematic viscosity is also dependent upon downhole temperatures and pressures.

The designed viscometer sensor package is preferably made from titanium alloy (e.g., Titanium 6-4) with a diaphragm having a thickness from preferably about 0.030 to about 0.040 inches. In one or more embodiments, the second magnet and electrical coil assembly is used to propel the diaphragm vibration at a carrier frequency in the 0 to 100 kHz range. A signal pick-up may use the same electrical coil or another electrical coil to separate excitation and induction signals that actually reduce signal processing difficulties. The gap or distance between the first and second magnets and induced eddy current will transform diaphragm vibration or displacement into a measurable voltage signal for processing, while the first magnet, which is attached to diaphragm internal surface, is used to transmit the second magnet electromagnetic force to the diaphragm. In order for the electrical coil to pick up a diaphragm vibrating signal, the first magnet may be made from a permanent magnet or from a ferromagnetic material, such as Cobalt, Nickel, Iron, or $Fe_2O_3$, or any strong ferromagnetic material with a Curie temperature higher than 200° C. or higher than the downhole temperature. In a specific embodiment, the ferromagnetic material is lanthanide elements-based rare-earth magnets.

Figure 2A:
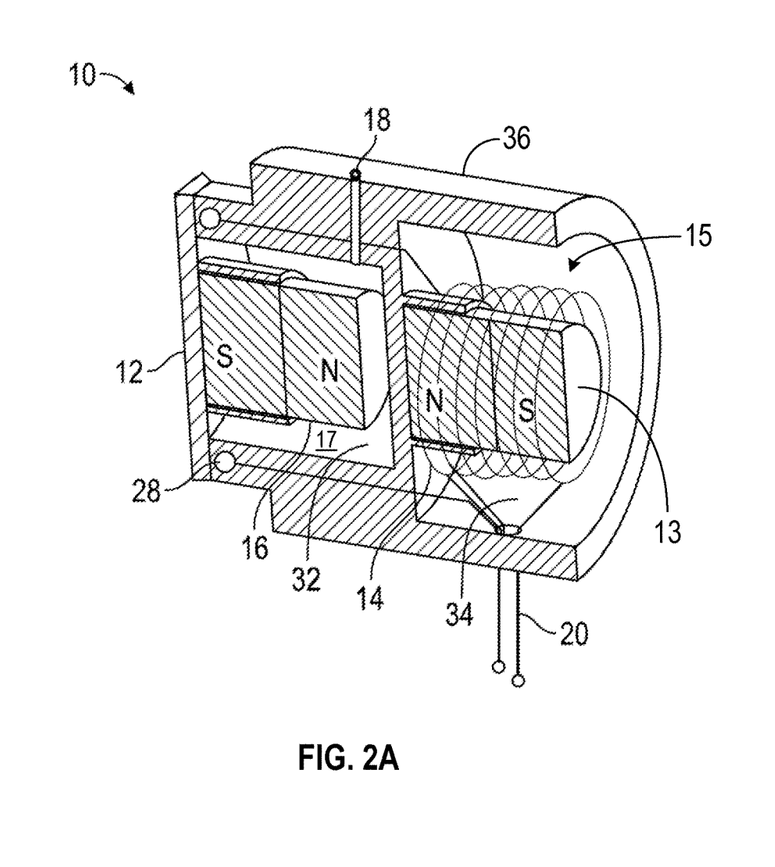
FIGS. 2A and 2B show cross-sectional perspective and side views, respectively, of exemplary embodiments embodiment of a viscometer sensor.
Figure 2B:
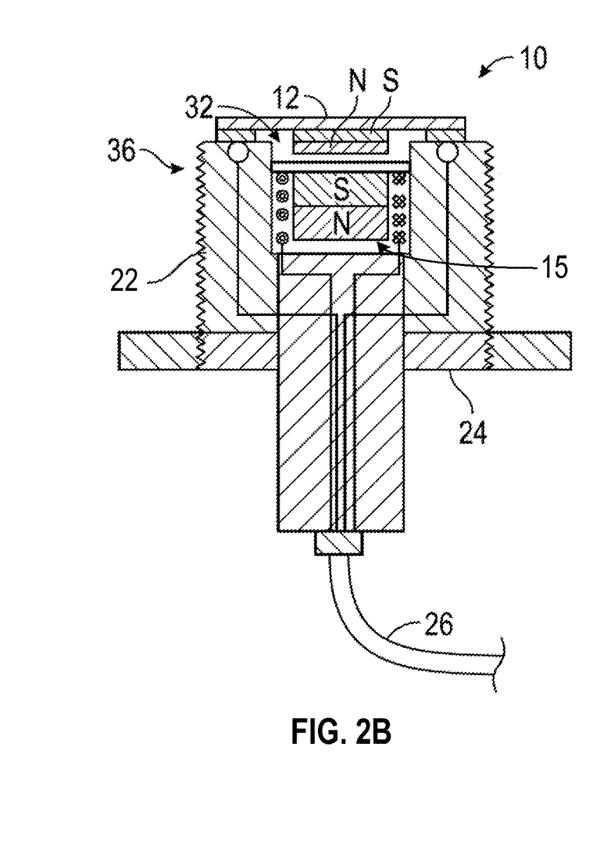

FIGS. 2A and 2B show exemplary embodiments of the viscometer sensor package 10 with a diaphragm 12 made of a titanium alloy (Ti-alloy) or similar material that is hermetically attached in front of the sensor package. The viscometer sensor package 10 has a generally cylindrical body or housing 36 that may also be made of Ti-alloy or similar material. A first magnet 16 having north (N) and south (S) poles is provided in a first cavity 32 attached to the diaphragm 12, which can vibrate at its natural frequency. A second magnet 13 having north (N) and south (S) poles and an electrical coil 14 is provided in a second cavity 34. The second magnet 13 (the poles of which are oriented to oppose the first magnet 16) and the electrical coil 14 form an electromagnetic driving assembly 15 that may be used to drive the first magnet 16 to produce vibrations in the diaphragm 12. The resulting voltage signal induced by the vibrations may then be measured for determining diaphragm vibration resonant frequency and decay characteristics. In some embodiments, the first cavity 32 may be filled with a silicon oil 17 that can effectively balance the pressure difference resulting from the downhole environment. The second magnet and electrical coil assembly 15 is sealed in the second cavity 34 so that a gap separates the second magnet 13 from the first magnet 16. An alternating driving current from an external current source 20 may be used to cause the second magnet and electrical coil assembly 15 to produce an alternating electromagnetic force to push and pull the first magnet 16. A pressure balance hole 18 may also be incorporated in the first cavity 32. The same electrical coil 14 may be used for both vibration excitation and as part of a signal pickup assembly, but it is of course possible for the signal pickup assembly to comprise another, second coil (not expressly shown) without departing from the scope of the disclosed embodiments. Signal pickup and processing may be performed using any suitable algorithm or process, including, for example, a Fast Fourier Transform based process. In some embodiments, the viscometer sensor package 10 also has threads 22 around its cylindrical body or housing 36 and a mounting plate or flange 24 for securing the sensor package 10 to other downhole tools and equipment. In a preferred embodiment, a titanium alloy is used for the diaphragm 12 with a ferromagnetic magnet attached as the first magnet 16 for downhole corrosive fluid viscosity analysis. In some embodiments, an electric cable 26 may be used to transmit the detected signal from the sensor 10 to an electric circuit board or other processing means. For high accuracy fluid viscosity analysis, a pair of thermocouples 28 may be installed near the front of the sensor package 10 for providing real-time fluid temperature data that may be used to distinguish potential hydrocarbon variation from thermal variation.

As mentioned above, to make the sensor package 10 feasible at 20 kpsi downhole condition, the first cavity 32 may be used as a differential pressure cavity by filling it with, for example, silicon oil 17 and providing a pressure balance hole 18. In one embodiment, the pressure balance hole 18 may be a tiny bellow tube that can transfer pressure to balance out the pressure inside the first cavity 32 with the pressure of the downhole environment. Preferably, the differential pressure will be greatly reduced, for example, to below 10 kpsi range, but higher than a bubble point pressure, $P_{bubble}$.

Figure 3:
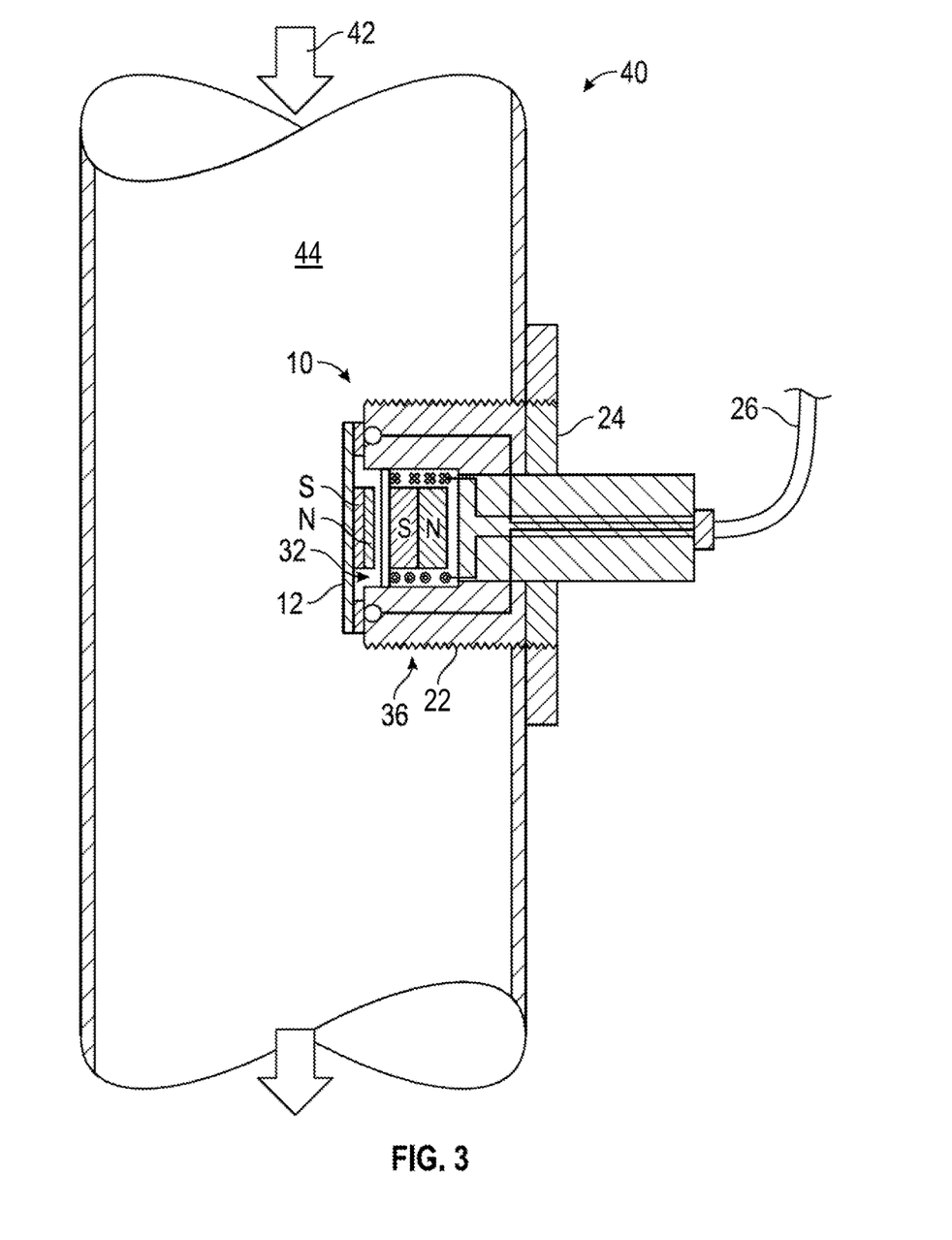
FIG. 3 shows a cross-sectional side view of an installation method of an exemplary viscometer sensor from a downhole sampling tool flowline.

FIG. 3 shows an exemplary installation 40 using the viscometer sensor package 10 disclosed herein in the form of a probe-like head that can be easily screwed into a downhole sampling tool flowline. Formation fluid 42 is pumped from the formation to a sampling tool 44 and the viscometer sensor 10 can be installed in any appropriate location, for example, after a Flow-Control Pump-Out Section module, as equipped in a reservoir description tool for formation fluid in-situ sampling analyses. Because a sampling tool may have a length of several meters with potential thermal gradient, a pair or several of such viscometer sensors 10 may be installed at the fluid entrance and exit ends to get reliable real-time fluid viscosity analyses. Such viscosity analyses may be affected by temperature as follows:

$$\Delta \eta = \exp(a - b*\ln(T_1)) - \exp(a - b*\ln(T_2)), \quad (4)$$

where a and b are calibration constants. In another embodiment, when the downhole sampling tool temperature, distributed along the body, can be modulated by an electric heating mechanism, a simple downhole viscosity fluid calibration method may be provided by varying several temperature values from the same fluid and the obtained viscosity may be fitted to the following equation:

$$\ln(\eta_i) = a - b*\ln(T_i), \quad (5)$$

where i represents the number of the varied temperature values, and ln ($\eta$) is expressed in natural logarithmic scale value. The $T_i$ represents fluid temperature determined by sampling tool heating mechanism.

Figure 4:
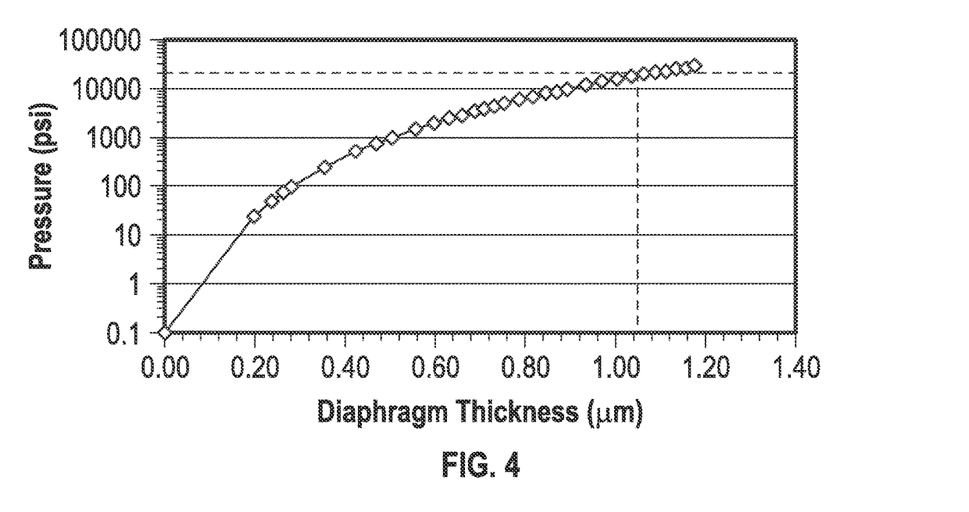
FIG. 4 shows a diagram of the minimum diaphragm thickness for an embodiment of the viscometer sensing package versus downhole pressure.

For a no-pressure compensated design, the minimum diaphragm thickness, h, for surviving 20 kpsi is about 0.040 inches (about 1.00 mm). For differential pressure design at 5 kpsi, the required thickness, h, can be reduced to 0.030 inches (about 0.75 mm). In this way, the diaphragm thickness can be approximately expected as follows:

$$h(T) = R^{1/4} \sqrt{\frac{5(1-\mu^2)}{8\gamma(T)}} * \Delta \rho \quad (6)$$

where $\Delta P$ is the differential pressure from two sides of the diaphragm, R is the radius of the diaphragm, $\mu$ is the Poisson's ratio of the Ti-alloy, Y(T) is temperature dependent diaphragm Young modulus. FIG. 4 is a diagram that shows diaphragm thickness (horizontal axis) versus pressure (vertical axis). The dashed lines indicate the minimum diaphragm thickness that may be used for a miniaturized viscometer sensor having a Ti-alloy based diaphragm as a vibrating element to be able to measure the natural damping response. In general, smaller differential pressure enables a thinner diaphragm to be used and vibration may be excited using lower electromagnetic driving force.

Once a minimum diaphragm thickness is chosen, the corresponding resonant frequency is:

$$f(T) = \frac{\alpha}{4\pi} \sqrt{\frac{Y(T)}{3\varrho(T)(1-\mu^2)}} \left(\frac{h}{R^2}\right) \quad (7)$$

where $\alpha \approx 10.21$ is related to the vibrating mode parameter of the diaphragm, q(T) is the temperature dependent diaphragm material density, and h is thickness of the diaphragm.

Figure 5:
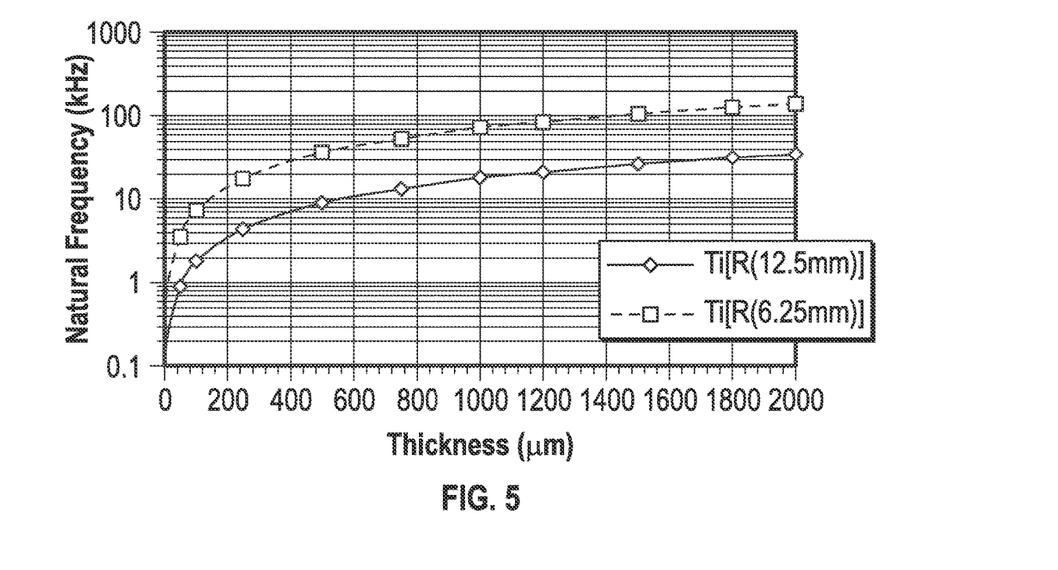
FIG. 5 shows a graph of resonant frequency versus diaphragm thickness for an embodiment of the viscometer sensing package.

FIG. 5 shows the calculated natural vibration frequency (vertical axis) for different diaphragm thicknesses (horizontal axis). A typical vibrating frequency will be ~10 kHz when the diaphragm thickness is about 150 μm for R=6.25 mm. Keeping the same diaphragm thickness, the resonant frequency is around 2 kHz for R=12.5 mm. The larger the diaphragm radius R, the lower the corresponding resonant frequency. However, the resonant frequency is more or less linearly shifted downward by its nonlinear temperature dependent Young modulus.

Figure 6:
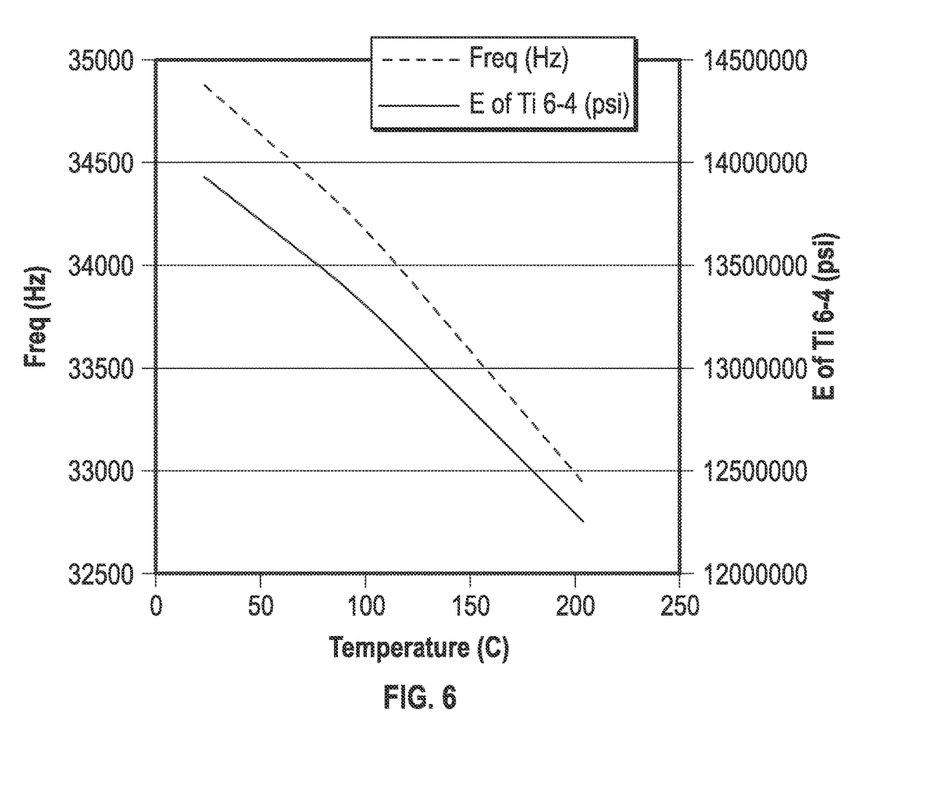
FIG. 6 shows a graph of Young elastic modulus related resonant frequency response to downhole temperature for an embodiment of the viscometer sensing package.

FIG. 6 represents a typical calculation for temperature dependent resonant frequency response from ambient temperature of about 24° C. to about 200° C. range with a diaphragm thickness of 750 μm. The resonant frequency downshift is about −6% up to about 200° C. It can be seen that the corresponding Young modulus decrease is a primary cause for resonant frequency downshift, which may be determined as follows:

$$f(T) = f(T_o) * \left(1 - \frac{\delta \cdot \Delta T}{2Y(T_o)}\right) \quad (8)$$

where $\delta$ is constant and $Y(T_o)$ is Young modulus at calibration temperature, $T_o$. This temperature dependent frequency shift can be embedded into the data process when the temperature is input from a thermometer or thermocouple sensor.

Figure 7:
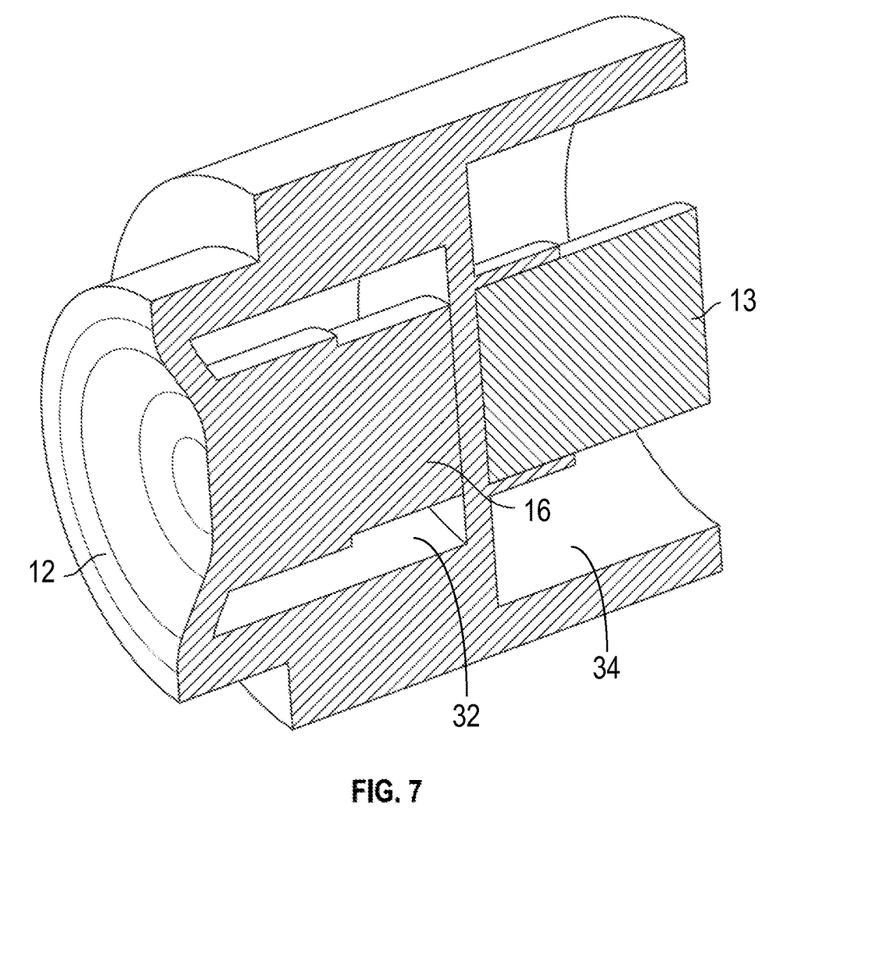
FIG. 7 shows cross-sectional perspective embodiments of vibrating mode resonant frequencies for an embodiment of the viscometer sensing package.

A further design consideration on the sensor package relates to the diaphragm vibrating modes distribution, as shown in FIG. 7. In one typical design case, the front diaphragm 12 vibrates at 34.87 kHz frequency, while the driving magnet/coil assembly 15 can vibrate at 40.4 kHz. To suppress this undesirable mode, the wall thickness of the cavity 32 may be increased so that its natural frequency is at least 5-10 times higher than the resonant frequency of the viscometer sensor package, namely, 35-40 kHz.

To excite the diaphragm vibration from the first magnet 16, the driving magnet and electrical coil assembly 15 is sealed in the second cavity 34. Alternating current will produce alternating electromagnetic force to vibrate the first magnet 16 attached diaphragm 12 for displacement in the flowing fluid. For example, the magnetic force generated by a 2 A current passing through a 1000 turn electrical coil 14 wound around 9.5 mm core 13 can be given by:

$$F = \frac{(F_m)^2 \mu_\sigma \mu_r A}{(2g^2)}, \quad (9)$$

where $F_m$=N*I, I=2 Amps, N=1000 turns, $\mu_0$=4π×10$^{-7}$, $\mu_r$=1, g=gap between first and second magnets=1 mm, and A=π×4.75$^2$. Thus, the calculated driving force F is about 180 N. The maximum displacement amplitude for a diaphragm of about 25 mm×0.75 mm made of Titanium 6-4 material can be predicted by:

$$\gamma_{max} = \frac{Wa^2}{16\pi D}, \text{ and } D = \frac{Et^3}{12(1-v^2)} \quad (10)$$

This will give maximum displacement amplitude of 140 μm, which is well within the measurable range. A time modulated signal may be used to excite the diaphragm vibration and damping response. At a predetermined time, the driving force is stopped, and the diaphragm vibrations allowed to naturally attenuate by fluid friction force. The time-domain diaphragm z-axial displacement may be determined by:

$$\psi(z) = \frac{3(1-\mu^2)\Delta P}{16Y(T)} \left(\frac{R^4}{h^3}\right) \quad (11)$$

Figure 8:
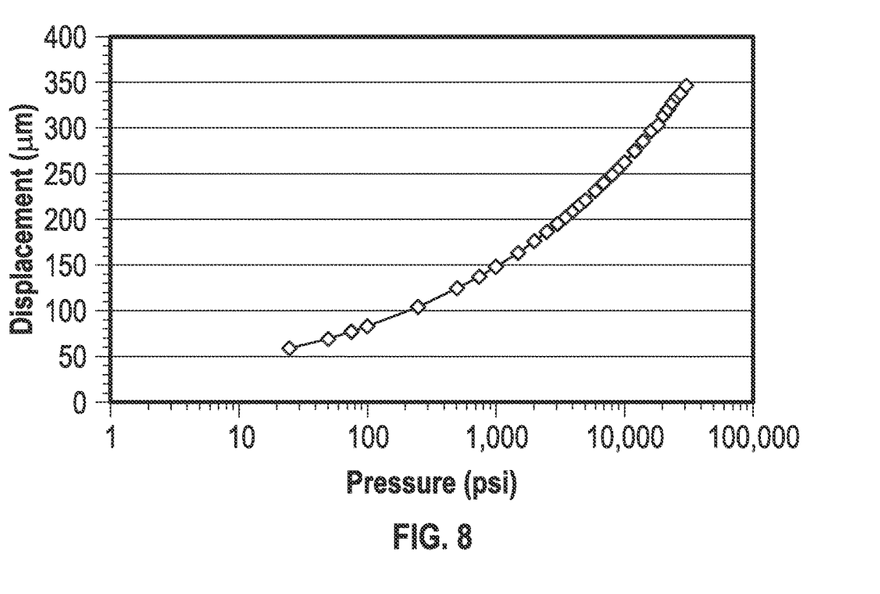
FIG. 8 shows a graph of diaphragm displacement amplitude versus differential pressure for an embodiment of the viscometer sensing package.

FIG. 8 shows the maximum diaphragm displacement predicted under different differential pressure for a viscometer sensor with a diaphragm having R=6.25 mm. For a given minimum diaphragm thickness h, radius R, and Young modulus Y(T), the displacement amplitude will be differential pressure dependent. As can be seen, the maximum displacement amplitude is about 0.012 inches (300 μm) for a differential pressure of 20 kpsi. However, this displacement amplitude will be reduced to less than 0.010 inches (250 μm) for a 5 kpsi differential pressure. At relatively low differential pressure conditions, the displacement amplitude may be reduced to 0.004 inches for ΔP<300 psi differential pressure, which is a more favorable high-frequency vibration.

As set forth above, the embodiments disclosed herein may be implemented in a number of ways. In general, in one aspect, the exemplary embodiments relate to a downhole formation fluid viscometer sensor. The downhole formation fluid viscometer sensor comprises, among other things, a generally cylindrical housing, a flexible diaphragm disposed on the generally cylindrical housing, and a first magnet attached to the flexible diaphragm within the cylindrical housing. The downhole formation fluid viscometer sensor further comprises a second magnet disposed a predefined distance from the first magnet within the cylindrical housing, an electric coil disposed around the second magnet within the cylindrical housing so as to drive the first magnet when the electric coil is energized(e.g., in the manner described herein), and a signal pickup assembly disposed within the housing and configured to pick up signals representing diaphragm vibrations from the first magnet. The electric coil forms part of the signal pickup assembly.

In some embodiments, the viscometer sensor may further comprise a first cavity adjacent the flexible diaphragm for housing the first magnet, silicon oil in the first cavity, a second cavity adjacent the first cavity for housing the second magnet and the electric coil, a pressure balance hole connecting the first cavity to an external environment, and/or threads and a mounting plate disposed on the cylindrical housing to allow the viscometer sensor to be secured to downhole tools and equipment.

In some embodiments, the diaphragm may be a titanium alloy, may have a thickness from preferably about 0.030 to about 0.040 inches, and/or may be hermetically sealed. In some embodiments, the second magnet and the electric coil propel the diaphragm vibration at a frequency from 0-100 kHz range, the first magnet may be a permanent magnet, a ferromagnetic magnet, or a rare-earth magnet. In some embodiments, an induced eddy current from the first magnet provides the signals representing diaphragm vibrations to the second magnet and the electric coil. In some embodiments, the viscometer sensor may further comprise software and data storage for driving the diaphragm vibrations and picking up the induced eddy current.

In general, in another aspect, the disclosed embodiments relate to a method of sensing fluid viscosity. The method comprises the steps of exciting an electromagnetic force to mechanically drive a first magnet using an electric coil around a second magnet to cause vibration of a diaphragm in a formation fluid, measuring a natural damping amplitude as a function of time of the vibration, measuring a corresponding voltage decay signal induced by the vibration, and determining a vibration resonant frequency using a Fast Fourier Transform process. In some embodiments, the viscometer sensor comprises a generally cylindrical housing, a flexible diaphragm disposed on the generally cylindrical housing, a first magnet attached to the flexible diaphragm within the cylindrical housing, a second magnet disposed a predefined distance from the first magnet within the cylindrical housing, an electric coil disposed around the second magnet within the cylindrical housing so as to drive the first magnet when the electric coil is energized (e.g., in the manner described above), and a signal pickup assembly disposed within the housing and configured to pick up signals representing diaphragm vibrations from the first magnet. The electric coil forms part of the signal pickup assembly.

In some embodiments, the method further comprises sensing downhole formation fluid kinematic viscosity and sensing dynamic viscosity by combining the viscometer sensor with a density sensor. In some embodiments, the step of sensing downhole formation fluid kinematic viscosity and sensing dynamic viscosity occurs in open hole wireline logging environments. In some embodiments, the step of sensing downhole formation fluid kinematic viscosity and sensing dynamic viscosities occurs in heavy oil production process.

In some embodiments, the viscometer sensor further comprises a first cavity adjacent the flexible diaphragm for housing the first magnet, a second cavity adjacent the first cavity for housing the second magnet and the electric coil, and/or silicon oil disposed in the first cavity. In some embodiments, the viscometer sensor further comprises pressure balance hole disposed through the cylindrical housing and connecting the first cavity to the formation fluid. In some embodiments, the diaphragm is made of a titanium alloy and/or is hermetically attached to the cylindrical housing.

Therefore, the present embodiments are well adapted to attain the ends and advantages mentioned as well as those that are inherent therein. The particular embodiments disclosed above are illustrative only, as the exemplary embodiments may be modified and practiced in different but equivalent manners apparent to those skilled in the art and having the benefit of the teachings herein.

Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments.

The exemplary embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps.

All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

While the disclosed embodiments have been described with reference to one or more particular implementations, those skilled in the art will recognize that many changes may be made thereto without departing from the spirit and scope of the description. Accordingly, each of these embodiments and obvious variations thereof is contemplated as falling within the spirit and scope of the claimed invention, which is set forth in the following claims.

What is claimed is:

1. A downhole formation fluid viscometer sensor comprising:
   a generally cylindrical housing;
   a flexible diaphragm disposed on the generally cylindrical housing;
   a first magnet attached to the flexible diaphragm within the cylindrical housing;
   a first cavity adjacent the flexible diaphragm for housing the first magnet;
   a pressure balance hole connecting the first cavity to an external environment;
   a second magnet disposed a predefined distance from the first magnet within the cylindrical housing;
   an electric coil disposed around the second magnet within the cylindrical housing so as to drive the first magnet when the electric coil is energized;
   a second cavity adjacent the first cavity for housing the second magnet and the electric coil; and
   a signal pickup assembly disposed within the housing and configured to pick up signals representing diaphragm vibrations from the first magnet, wherein the electric coil forms part of the signal pickup assembly;
   wherein an induced eddy current from the first magnet provides the signals representing diaphragm vibrations to the second magnet and the electric coil.

2. The viscometer sensor of claim 1 wherein the diaphragm is a titanium alloy diaphragm with a magnet attached thereto.

3. The viscometer sensor of claim 1 wherein the diaphragm has a thickness from about 0.030 to about 0.040 inches.

4. The viscometer sensor of claim 1 wherein the second magnet and the electric coil assembly propel the diaphragm to vibrate at a frequency from about 0 100 kHz.

5. The viscometer sensor of claim 1 further comprising threads around the cylindrical housing and a mounting plate disposed on the cylindrical housing, the threads and the mounting plate allowing the viscometer sensor to be secured to downhole tools and equipment.

6. The viscometer sensor of claim 1 wherein the diaphragm is hermetically attached to cylindrical housing.

7. The viscometer sensor of claim 1 further comprising silicon oil in the first cavity.

8. The viscometer sensor of claim 1 wherein the first magnet is one of: a permanent magnet, a ferromagnetic magnet, or a rare-earth magnet.

9. A method of sensing fluid viscosity comprising:
   disposing a viscometer sensor in a formation fluid, the viscometer sensor comprising:
   a generally cylindrical housing;
   a flexible diaphragm disposed on the generally cylindrical housing;
   a first magnet attached to the flexible diaphragm within the cylindrical housing;
   a second magnet disposed a predefined distance from the first magnet within the cylindrical housing;
   an electric coil disposed around the second magnet within the cylindrical housing so as to drive the first magnet when the electric coil is energized; and
   a signal pickup assembly disposed within the housing and configured to pick up signals representing diaphragm vibrations from the first magnet, wherein the electric coil forms part of the signal pickup assembly;
   exciting an electromagnetic force to mechanically drive the first magnet using the electric coil around the second magnet to cause vibration of the diaphragm in the formation fluid;
   measuring a natural damping amplitude as a function of time of the vibration;
   measuring a corresponding voltage decay signal induced by the vibration; and
   determining a vibration resonant frequency using Fast Fourier Transform.

10. The method of claim 9 further comprising sensing downhole formation fluid kinematic viscosity and sensing dynamic viscosity by combining the viscometer sensor with a density sensor.

11. The method of claim 10 wherein the step of sensing downhole formation fluid kinematic viscosity and sensing dynamic viscosity occurs in open hole wireline logging environments.

12. The method of claim 10 wherein the step of sensing downhole formation fluid kinematic viscosity and sensing dynamic viscosities occurs in heavy oil production processes.

13. The method of claim 9 wherein the viscometer sensor further comprises a first cavity adjacent the flexible diaphragm for housing the first magnet, a second cavity adjacent the first cavity for housing the second magnet the electric coil, and silicon oil disposed in the first cavity.

14. The method of claim 9 wherein the viscometer sensor further comprises a pressure balance hole disposed through the cylindrical housing and connecting a first cavity to the formation fluid.

15. The method of claim 9 wherein the diaphragm is a titanium alloy.

16. The method of claim 9 wherein the diaphragm is hermetically attached to the cylindrical housing.

* * * * *